United States Patent [19]

Zecher et al.

[11] Patent Number: 4,515,974

[45] Date of Patent: May 7, 1985

[54] PROCESS FOR THE PREPARATION OF FUMARIC ACID MONOESTERS

[75] Inventors: Wilfried Zecher; Rudolf Merten, both of Leverkusen, Fed. Rep. of Germany

[73] Assignee: Bayer Aktiengesellschaft, Leverkusen, Fed. Rep. of Germany

[21] Appl. No.: 392,037

[22] Filed: Jun. 25, 1982

[30] Foreign Application Priority Data

Jul. 11, 1981 [DE] Fed. Rep. of Germany ....... 3127432

[51] Int. Cl.³ .................... C07C 67/08; C07C 69/60; C07D 319/02; C07D 319/04; C07D 319/12; C07D 307/46

[52] U.S. Cl. .................... 549/372; 549/378; 549/416; 549/475; 549/484; 549/499; 560/190; 560/192; 560/193; 560/194; 560/196; 560/198; 560/201; 560/204; 544/171; 544/318; 544/319; 544/385; 544/408; 546/242; 546/243; 546/298; 548/225; 548/230; 548/232; 548/243; 548/301; 548/337; 548/363; 548/375; 548/351; 548/541; 548/543; 548/358

[58] Field of Search ............... 560/192, 193, 201, 204, 560/194, 196, 198, 190; 544/171, 318, 319, 385, 408; 546/242, 243, 298; 548/225, 230, 243, 301, 337, 351, 358, 363, 375, 541, 543, 232; 549/372, 378, 416, 475, 484, 499; 424/278, 285, 313

[56] References Cited

U.S. PATENT DOCUMENTS

| | | | |
|---|---|---|---|
| 2,254,382 | 9/1941 | Neher | 560/201 X |
| 2,764,609 | 9/1956 | Gamrath | 560/203 |
| 3,378,470 | 8/1968 | Kroll | 560/201 X |
| 3,475,483 | 10/1969 | Dowbenko | 560/203 |

Primary Examiner—Natalie Trousof
Assistant Examiner—Vera C. Clarke
Attorney, Agent, or Firm—Sprung, Horn, Kramer & Woods

[57] ABSTRACT

Fumaric acid monoesters can be prepared by introducing a hydroxyl compound at a rate corresponding to the progress of the reaction into a solution or a melt of maleic anhydride, which may optionally be substituted, if appropriate in the presence of a cis-trans catalyst. New fumaric acid monoesters can be formed by the process.

19 Claims, No Drawings

PROCESS FOR THE PREPARATION OF FUMARIC ACID MONOESTERS

BACKGROUND OF THE INVENTION

The invention relates to a process for the preparation of fumaric acid monoesters from maleic anhydride.

It is known that fumaric acid monoalkyl esters are obtained by partially esterifying fumaric acid with alcohols (Chem. Ber. 30, 2651 (1897)). Further known routes of preparation are the partial hydrolysis of fumaric acid diesters and the cis-trans re-arrangement of maleic acid monoesters (German Patent Specification No. 1,291,739 and German Offenlegungsschrift 2,130,300).

SUMMARY OF THE INVENTION

A process for the preparation of fumaric acid monoesters has been found, which is characterized in that a hydroxyl compound is introduced, within the temperature range of 100° C. to 220° C. and at a rate corresponding to the progress of the reaction, into a solution or melt of maleic anhydride, which may optionally be substituted, if appropriate in the presence of a cis-trans catalyst.

The process according to the invention is surprising, since, under the reaction conditions according to the invention, it would be expected that the half-esters would undergo cleavage again and, furthermore, that a considerable proportion of diesters would be formed.

In comparison with known processes, good yields and very short reaction times are achieved in accordance with the invention. A factor which is particularly advantageous is that, when volatile alcohols are employed, it is possible to avoid working under pressure.

The process according to the invention can be illustrated, for example, by means of the following equation:

$$HC\!=\!\!=\!\!CH \text{ (maleic anhydride)} + CH_3OH \longrightarrow$$

$$CH_3O-\overset{O}{\underset{\|}{C}}-CH\!=\!CH-\overset{O}{\underset{\|}{C}}-OH$$

trans

DETAILED DESCRIPTION OF THE INVENTION

The maleic anhydride used for the process according to the invention can be substituted by alkyl, aryl or halogen.

In this context alkyl is preferably lower alkyl ($C_1$ to about $C_6$) and particularly preferentially methyl and ethyl.

Aryl is preferably phenyl, tolyl and xylyl.

Halogen is preferably fluorine, chlorine, bromine or iodine and particularly preferentially chlorine.

Maleic anhydrides which are particularly preferred for the process according to the invention are those of the formula (I)

$$\begin{array}{c} R^1-C-C\overset{O}{\underset{\diagdown}{\nearrow}} \\ \| \quad\quad O \\ R^2-C-C\overset{\diagup}{\underset{\diagdown}{\nwarrow}} \\ O \end{array} \quad (I)$$

in which $R^1$ and $R^2$ are identical or different and denote hydrogen, lower alkyl, aryl or halogen.

The following maleic anhydrides may be mentioned as examples: maleic anhydride, dimethylmaleic anhydride, monoethyl maleic anhydride, monophenyl maleic anhydride, dichloromaleic anhydride and monobromomaleic anhydride.

In particular, unsubstituted maleic anhydride is preferred for the process according to the invention.

Hydroxyl compounds for the process according to the invention can be compounds of the formula (II)

$$R^3(OH)_n \quad (II)$$

in which $R^3$ denotes alkyl, alkenyl, alkinyl, aralkyl, aryl, cycloalkyl, a 5-membered or 6-membered heterocyclic radical having 1 or 2 oxygen or nitrogen atoms, or the radical of a polyether, polyester, polyurea, polyurethane, polyimide or polyhydantoin and n represents one of the numbers 1, 2 or 3.

In accordance with the invention, alkyl in this context ($R^3$) can be a straight-chain or branched hydrocarbon having 1 to 24 carbon atoms, preferably 1 to 12 carbon atoms. A lower alkyl radical having 1 to about 6 carbon atoms is particularly preferred. The following alkyl radicals may be mentioned as examples: methyl, ethyl, propyl, isopropyl, butyl, isobutyl, pentyl, isopentyl, hexyl and isohexyl.

In accordance with the invention, alkenyl in this context ($R^3$) can be a straight-chain or branched hydrocarbon which has one or more, preferably one, double bond and which contains 3 to 24, preferably 3 to 12, carbon atoms. A lower alkenyl radical having 3 to about 6 carbon atoms is particularly preferred. The following alkenyl radicals may be mentioned as examples: 2-propenyl, isobutenyl, 2-methyl-3-butenyl and 9-octadecenyl.

In accordance with the invention, alkinyl in this context ($R^3$) can be a straight-chain or branched hydrocarbon which has one or more, preferably one, triple bond and can contain 3 to 24, preferably 3 to 12, carbon atoms. A lower alkinyl radical having 3 to about 6 carbon atoms is particularly preferred. The following alkinyl radicals may be mentioned as examples: 2-propinyl, 3-butin-2-yl, 2-methyl-3-butinyl and 9-octadecenyl.

In accordance with the invention, aralkyl can in this context ($R^3$) contain 1 to 6, preferably 1 or 2, carbon atoms in the aliphatic part and 6 to 12, preferably 6 to 10, carbon atoms in the aromatic part. The following aralkyl radicals may be mentioned as examples: benzyl, phenylethyl and phenylpropyl.

In accordance with the invention, aryl can in this context ($R^3$) contain 6 to 12 carbon atoms. Preferred aryl radicals are phenyl, biphenyl and naphthyl. The phenyl radical is particularly preferred.

In accordance with the invention, cycloalkyl can in this context ($R^3$) be a cyclic aliphatic hydrocarbon having 3 to 10, preferably 5 to 7, carbon atoms. Cyclopentyl and cyclohexyl are particularly preferred. The following cycloalkyl radicals may be mentioned as examples: cyclopropyl, cyclobutyl, cyclopentyl, cyclohexyl, cycloheptyl, cyclooctyl, cyclononyl and cyclodencyl.

A 5-membered or 6-membered heterocyclic radical having 1 or 2 oxygen atoms can preferably be a furan or dioxane ring which is optionally linked to the hydroxyl group via alkylene ($C_1$ to $C_6$).

In accordance with the invention, a polyester radical can in this context ($R^3$) be built up from the monomers ethylene oxide or propylene oxide. In accordance with the invention, the polyether radicals have a molecular weight within the range from 75 to 20,000, preferably from 500 to 5,000.

In accordance with the invention, a polyether radical can in this context ($R^3$) be built up from the monomeric units of phthalic acid, isophthalic acid, terephthalic acid, adipic acid and ethylene glycol, neopentyl glycol, trimethylolpropane and glycerol. In general, the polyester radicals according to the invention have a molecular weight within the range from 200 to 30,000, preferably from 300 to 10,000.

Similarly, the radical $R^3$ can also represent a polyurea radical, a polyurethane radical, a polyimide radical or a polyhydantoin radical. In general, these radicals have a molecular weight within the range from 500 to 30,000.

The radicals $R^1$ which have been mentioned can, of course, be substituted by any radicals which do not undergo change under the conditions according to the invention. The following radicals may be mentioned as examples: halogen, nitro, alkyl, alkoxy, aroxy, alkylmercapto, arylmercapto, sulphonic acids and carboxylic acids and esters thereof.

Hydroxyl compounds which are preferred for the process according to the invention are compounds of the formula (III)

$$R^4(OH)_n \quad \text{(III)}$$

in which $R^4$ denotes alkyl having 1 to 24 carbon atoms, alkenyl having 3 to 24 carbon atoms, alkinyl having 3 to 24 carbon atoms, aralkyl having 1 to 6 carbon atoms in the aliphatic part and 6 to 12 carbon atoms in the aromatic part, aryl having 6 to 12 carbon atoms or cycloalkyl having 5 to 10 carbon atoms, and n has the abovementioned meaning.

The following hydroxyl compounds may be mentioned as examples: methanol, ethanol, n-butanol, isobutanol, tert.-butanol, hexanol, eicosanol, allyl alcohol, propargyl alcohol, cyclohexanol, phenol and benzyl alcohol.

Aliphatic hydroxyl compounds, such as methanol, ethanol, isopropanol, allyl alcohol and propargyl alcohol are particularly preferred for the process according to the invention.

The process according to the invention can advantageously be carried out in the process of a cis-trans catalyst. These are catalysts which accelerate a cis-trans re-arrangement (Theoretische Grundlagen der organischen Chemie (Theoretical Principles of Organic Chemistry), 2nd Edition, Volume 1, page 477 (1956)). The following cis-trans catalysts may be mentioned as examples: halogens, such as fluorine, chlorine, bromine and iodine; acids, for example mineral acids, such as hydrogen halide acids, and organic acids, such as, for example, p-toluenesulphonic acid, acid halides, such as acetyl chloride and benzenesulphochloride, titanium tetrachloride, boron trifluoride, metals, such as platinum, the cations of the alkali metals, such as the sodium ion, amines, such as triethylamine, morpholine, piperidine or aniline, ammonium salts, such as ammonium chloride, thiourea and phosphorus compounds, such as triethyl phosphite and triphenylphosphine. Iodine is particularly preferred as a cis-trans catalyst for the process according to the invention.

The process according to the invention is carried out in a solution or melt of the reactants. It is possible to use customary solvents which do not react or form only loose addition compounds under the reaction conditions. The following may be mentioned as examples of solvents: halogenated hydrocarbons, such as chloroform or carbon tetrachloride, esters, such as alkyl ester of acetic acid and benzoic acid, lactones, such as butyrolactone and caprolactone, ketones, such as isobutyl methyl ketone, acetophenone and cyclohexanone, ethers, such as glycol monomethyl ether-acetate, diethylene glycol monomethyl ether and diethylene glycol dimethyl ether, substituted amides, such as dimethylformamide and N-methylpyrrolidone, nitriles, sulphoxides and sulphones.

Solvents which are particularly preferred for the process according to the invention are those of low polarity, such as, for example, higher aliphatic compounds, tetralin, decalin and alkylaromatic compounds. It is, of course, also possible to use as solvents mixtures of the compounds which have been mentioned individually. However, it is also possible in accordance with the invention to dispense with the solvent and to carry out the reaction in a melt of the reactants.

The process according to the invention is customarily carried out under normal pressure. However, it is also possible to carry out the process according to the invention under a diminished pressure or under an excess pressure.

The process according to the invention can be carried out either discontinuously or continuously.

It is preferable to carry out the reaction according to the invention by initially taking the acid anhydride and the catalyst in a melt or in one of the solvents listed and adding the alcohol dropwise or introducing it undiluted or in solution at temperatures of 100° C. to 220° C., preferably 150° C. to 180° C., at such a rate that a fairly sharp increase or decrease in the reaction temperature, perhaps expressed by excessive reflux in the case of readily volatile alcohols, is avoided. The course of the reaction can be followed by the IR spectrum via the carbonyl bands of the cyclic carboxylic acid anhydride and of the half-ester. In general, one equivalent of the hydroxyl compound is employed per mol of acid anhydride, but deviations from this ratio are also advantageous occasionally.

Fumaric acid monoesters of the formula (IV)

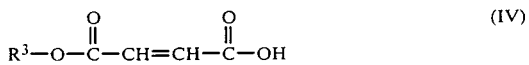

in which $R^3$ has the abovementioned meaning, can be prepared by the process according to the invention.

The fumaric acid esters prepared by the process according to the invention are starting materials for the preparation of plastics of the polyhydantoin type.

In addition, the use of fumaric acid esters as comonomers for the preparation of solution and emulsion copolymers is known from German Offenlegungsschrift No. 2,552,634.

Fumaric acid alkinyl esters are new. Special mention may be made of compounds, according to the invention, of the formula (V)

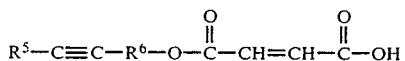

in which $R^5$ represents hydrogen, alkyl having 1 to 24 carbon atoms, aralkyl having 1 to 6 carbon atoms in the aliphatic part and 6 to 12 carbon atoms in the aromatic part or aryl having up to 12 carbon atoms and $R^6$ represents a divalent aliphatic radical having 1 to 24 carbon atoms or araliphatic radical having 1 to 6 carbon atoms in the aliphatic part and 6 to 12 carbon atoms in the aromatic part.

The scope of meanings of the alkyl, aralkyl and aryl radicals mentioned in formula (V) corresponds to the scope defined above for formula (II).

In accordance with the invention, fumaric acid alkinyl esters of the formula (VI)

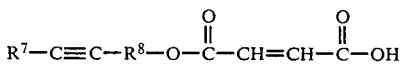

in which $R^7$ denotes hydrogen, lower alkyl, benzyl or phenyl and $R^8$ represents a bivalent aliphatic radical having 1 to 6 carbon atoms, are particularly preferred.

Monopropargyl fumarate is particularly preferred.

The new fumaric acid alkinyl esters can be reacted particularly advantageously to give polyheterocyclic compounds. Moreover, they have an activity against fungi and psoriasis vulgaris.

EXAMPLE 1

Monoethyl fumarate 736 g of ethanol are added dropwise, at 160° C. and in the course of about 1 hour, to a solution of 1,568 g of maleic anhydride and 16 g of iodine, as catalyst, in 1,600 g of a technical mixture of alkylaromatic compounds, as solvent. Stirring is then continued for a further half hour. The reaction mixture is filtered while still hot and the filtrate is fractionated on a column. 1,810 g of monoethyl fumarate of melting point 106°–108° C. are obtained at 0.4 mbar/106°–108° C.

Analysis: Calculated C: 50.0, H: 5.6 %, Found C: 50.3, H: 5.8 %,

EXAMPLE 2

Monisopropyl fumarate 882 g of maleic anhydride, 2.9 g of iodine, 1 g of aniline and 1 g of hydroquinone are dissolved in 1750 g of a technical mixture of alkylaromatic compounds, as solvent, and the solution is heated to 160° C. 567 g of isopropanol are then added dropwise at this temperature in the course of 1.5 hours and stirring is then continued for a further half hour. Small quantities of fumaric acid are removed from the reaction mixture by filtration. Distillation of the filtrate on a silver jacketed column gives 1,110 g of monoisopropyl fumarate of melting point 50°–51° C. at 0.14 mbar/100°–102° C.

Analysis: Calcuated: C: 53.2; H: 6.3 %, Found: C: 53.4; H: 6.2 %.

EXAMPLE 3

Monododecyl fumarate 744 g of dodecanol are added dropwise, at 160° C., to a solution of 392 g of maleic anhydride and 4 g of iodine in 400 g of a technical mixture of alkylaromatic compounds, as solvent. The reaction mixture is filtered while it is still hot. 820 g of dodecyl fumarate crystallize out from the filtrate in colourless crystals of melting point 80°–82° C.

Analysis: Calculated: C: 67.6; H: 9.9%; Found: C: 67.6;H: 9.8%;

EXAMPLE 4

Monomethyl fumarate 320 g of methanol are added dropwise, at 160° C., to 1000 g of a technical mixture of alkylaromatic compounds, as solvent, 980 g of maleic anhydride and 10 g of iodine. The reaction mixture is filtered while it is hot. On cooling, monomethyl fumarate crystallizes out in colourless crystals. Recrystallization from toluene gives 857 g of pure monomethyl fumarate of melting point 142°–144° C.

Analysis: Calculated: C: 46.2; H: 4.6%; Found; C: 46.2; H: 4.6%;

EXAMPLE 5

Monobenzyl fumarate 216 g of benzyl alcohol are added dropwise, at 160° C. and in the course of 45 minutes, to 200 g of a technical mixture of alkylaromatic compounds, as solvent, 196 g of maleic anhydride and 2 g of iodine. The mixture is then filtered while hot and filtered again after cooling and the filter residue is recrystallized from acetonitrile. Monobenzyl fumarate is obtained in colourless crystals of melting point 108°–110° C.

Analysis: Calculated: C: 64.1; H: 4.9%; Found: C: 64.2; H: 4.9%.

EXAMPLE 6

Monocyclohexyl fumarate 200 g of cyclohexanol are added dropwise, at 160° C. and in the course of 50 minutes, to a solution of 196 g of maleic anhydride and 2 g of iodine in 200 g of a technical mixture of alkylaromatic compounds, as solvent. The reaction mixture is filtered while hot and evaporated in a waterpump vacuum and the residue is recrystallized from light petroleum ether/toluene. Cyclohexyl fumarate is obtained in colourless crystals of melting point 86°–88° C.

Analysis: Calculated: C: 60.6; H: 7.1%; Found: C: 60.7, H: 7.1 %.

EXAMPLE 7

Monoallyl fumarate 196 g of maleic anhydride and 2 g of iodine are dissolved in 200 g of a technical mixture of alkylaromatic compounds, as solvent. 116 g of allyl alcohol are added dropwise at 160° C. and in the course of one hour. The mixture is then filtered while hot. On cooling, monoallyl fumarate crystallizes out and is filtered off and recrystallized from light petroleum ether. Colourless crystals of melting point 66°-67° C. are obtained.

Analysis: Calculated: C: 53.9; H: 5.1 %, Found: C: 53.9; H: 5.1 %.

EXAMPLE 8

Mono-1,4-butyl bis-fumarate 90 g of butane-1,4-diol are added dropwise, at 160° C., to 200 g of a technical mixture of alkylaromatic compounds, as solvent, 196 g of maleic anhydride, 2 g of iodine and 1 g of ammonium chloride. Stirring is continued for a further 30 minutes at 160° C., the product is filtered off after cooling and the bis-ester is obtained, after recrystallization from acetonitrile/dimethylformamide, as a white crystalline substance of melting point 172°–174° C.

Analysis: Calculated: C: 50.4; H: 4.9%, Found: C: 50.5; H: 4.9%,

EXAMPLE 9

Mono-1,3-dioxane-5-ethyl-5-methyl fumarate 292 g of 1,3-dioxane-5-ethyl-5-methanol are introduced, in portions at 160° C. and in the course of 2 hours, into a solution of 196 g of maleic anhydride and 2 g of iodine in 200 g of a technical mixture of alkylaromatic compounds, as solvent. The reaction mixture is filtered at 120° C. in order to remove solid constituents and the filtrate is then evaporated in vacuo. Recrystallization from 1:1 toluene/cyclohexane gives the monoester, which has a melting point of 77°–78° C.

Analysis: Calculated: C: 54.1; H: 6.6%; Found: C: 54.0; H: 6.6%

EXAMPLE 10

Monopropargyl fumarate 112 g of propargyl alcohol are added dropwise at 160° C. to 380 g of a technical mixture of alkylaromatic compounds, as solvent, 192 g of maleic anhydride, 1.9 g of iodine and 1 g of ammonium chloride. On cooling, the monoester is precipitated and, after being filtered off, it is recrystallized from acetonitrile and toluene. This gives pure monopropargyl fumarate, which has a melting point of 102°–103° C.

Analysis: Calculated C: 54.6; H: 3.9%; Found: C: 54.4; H: 3.9%.

What is claimed is:

1. A process for the preparation of a fumaric acid monoester which comprises contacting in the presence of a cis-trans catalyst an unsubstituted or substituted maleic anhydride in the form of a solution or in the form of a melt thereof with a hydroxyl compound at a temperature in the range of 100° C. to 220° C.

2. A process according to claim 1, wherein the hydroxyl compound is added at a rate corresponding to the progress of the reaction.

3. A process according to claim 1, wherein the hydroxyl compound is an aliphatic alcohol.

4. A process according to claim 1, wherein the cis-trans catalyst is a halogen or an acid or the ammonium salt thereof or an acid halide.

5. A process according to claim 1, wherein the cis-trans catalyst is iodine.

6. A process according to claim 1, wherein the hydroxyl compound has the formula $$R^3(OH)_n \quad (II)$$

in which
R$^3$ denotes alkyl, alkenyl, alkinyl, aralkyl, aryl, cycloalkyl, a 5-membered or 6-membered heterocyclic radical having 1 or 2 oxygen or nitrogen atoms, or the radical of a polyether, polyester, polyurea, polyurethane, polyimide or polyhydantoin and
n represents one of the numbers 1, 2 or 3.

7. A process according to claim 1, wherein the hydroxyl compound is one of the formula $$R^4(OH)_n \quad (III)$$

in which
R$^4$ denotes alkyl having 1 to 24 carbon atoms, alkenyl having 3 to 24 carbon atoms, alkinyl having 3 to 24 carbon atoms, aralkyl having 1 to 6 carbon atoms in the aliphatic part and 6 to 12 carbon atoms in the aromatic part, alkyl having 6 to 12 carbon atoms or cycloalkyl having 5 to 10 carbon atoms, and
n is one of the numbers 1, 2, or 3.

8. A process according to claim 1, wherein the hydroxyl compound is selected from the group consisting of methanol, ethanol, n-butanol, isobutanol, tert.-butanol, hexanol, eicosanol, allyl alcohol, propargyl alcohol, cycolhexanol, phenol and benzyl alcohol.

9. A process according to claim 1, wherein the process is carried out by reacting said maleic anhydride in the form of a solution thereof.

10. A process according to claim 1, wherein said maleic anhydride is in the form of a melt.

11. A process according to claim 1, wherein said maleic anhydride is substituted with a substituent selected from the group consisting of alkyl, aryl and halogen.

12. A process according to claim 1, wherein said unsubstituted or substituted maleic anhydride is selected from the group consisting of maleic anhydride, dimethyl maleic anhydride, monoethyl maleic anhydride, monophenyl maleic anhydride, dichloromaleic anhydride and monobromo maleic anhydride.

13. A process according to claim 1, wherein the hydroxy compound is an alcohol and the temperature range is 150° to 180° C.

14. A process according to claim 6, wherein said 5-membered or 6-membered heterocyclic radical having 1 or 2oxygen atoms is furan or dioxane.

15. A process according to claim 1, wherein the process is conducted under normal pressure.

16. A fumaric acid alkinyl monoester of the formula $$R^5-C\equiv C-R^6-O-\overset{O}{\underset{\|}{C}}-CH=CH-\overset{O}{\underset{\|}{C}}-OH$$

in which
R$^5$ denotes hydrogen, alkyl having 1 to 24 carbon atoms, aralkyl having 1 to 6 carbon atoms in the aliphatic part and 6 to 12 carbon atoms in the aromatic part, or aryl and
R$^6$ represents an araliphatic radical having 1 to 6 carbon atoms in the aliphatic part and 6 to 12 carbon atoms in the aromatic part.

17. A fumaric acid alkinyl monoester of the formula $$R^5-C\equiv C-R^6-O-\overset{O}{\underset{\|}{C}}-CH=CH-\overset{O}{\underset{\|}{C}}-OH$$

in which
- $R^5$ denotes aralkyl having 1 to 6 carbon atoms in the aliphatic part and 6 and 12 carbon atoms in the aromatic part, or aryl and
- $R^6$ represents a divalent aliphatic radical having 1 to 24 carbon atoms or an araliphatic radical having 1 to 6 carbon atoms in the aliphatic part and 6 to 12 carbon atoms in the aromatic part.

18. A process for the preparation of a fumaric acid monoester comprising conducting a reaction at a temperature in the range of 100° to 200° C. with a reaction mixture consisting essentially of an unsubstituted or substituted maleic anhydride in the form of a solution or in the form of a melt thereof, a hydroxyl compound and a cis-trans catalyst selected from the group consisting of a halogen, an acid and an ammonium salt thereof.

19. A process according to claim 18, wherein said catalyst is a halogen and wherein said halogen is iodine.

* * * * *